United States Patent

Franciose

[11] Patent Number: 5,142,558
[45] Date of Patent: Aug. 25, 1992

[54] METHOD AND APPARATUS FOR DETERMINING THE SUCCESS OF A PTCA PROCEDURE

[75] Inventor: Barbara D. Franciose, Elk Grove Village, Ill.

[73] Assignee: Siemens Gammasonics, Inc., Hoffman Estates, Ill.

[21] Appl. No.: 692,082

[22] Filed: Apr. 26, 1991

Related U.S. Application Data

[63] Continuation-in-part of Ser. No. 546,473, Jun. 29, 1990.

[51] Int. Cl.⁵ .............................................. H05G 1/64
[52] U.S. Cl. ...................................... 378/99; 378/98; 358/111
[58] Field of Search ...................... 378/99, 98; 358/111

[56] References Cited

U.S. PATENT DOCUMENTS 4,878,115 10/1989 Elion .................................. 358/111

Primary Examiner—Janice A. Howell
Assistant Examiner—Don Wong
Attorney, Agent, or Firm—Mark H. Jay

[57] ABSTRACT

A control panel, which includes a programmable electroluminescent touch screen, is mounted so as to be operable by the radiologist during a PTCA procedure. The system has the capability of displaying, for comparison purposes, synchronized comparable images of the arterial blood flow before and after the PTCA procedure. Synchronized image is achieved by adding or deleting video frames from the end of a patient's cardiac cycle.

9 Claims, 4 Drawing Sheets

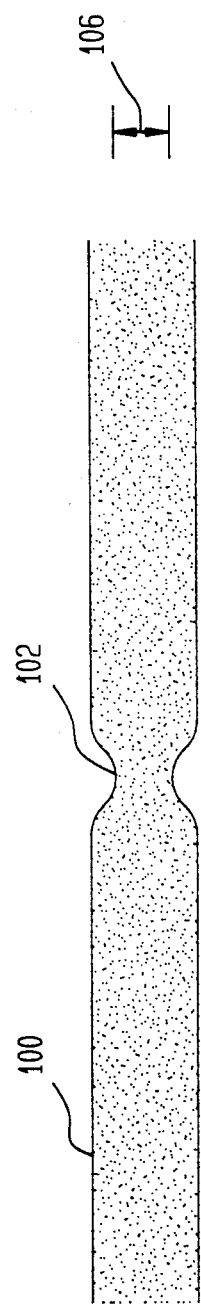
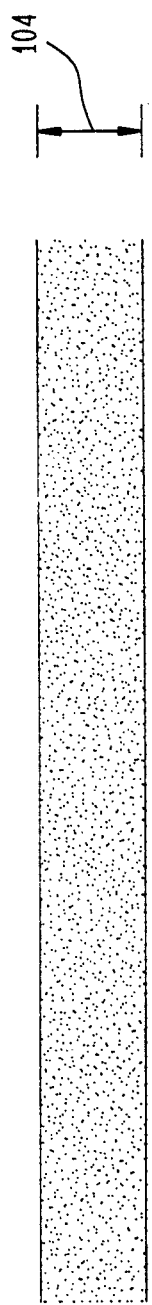
FIG. 2A
FIG. 2B

METHOD AND APPARATUS FOR DETERMINING THE SUCCESS OF A PTCA PROCEDURE

CROSS-REFERENCE TO RELATED APPLICATIONS

This application is a continuation-in-part of commonly-owned copending prior application Application No. 07/546,473, filed June 29, 1990. The entire disclosure of this prior application, including the drawings, is hereby incorporated herein as if fully set forth.

BACKGROUND OF THE INVENTION

The above-referenced parent application relates to X-ray apparatus which is used during a surgical procedure known as PTCA, or percutaneous transluminal coronary angioplasty. The apparatus therein described is specially adapted to facilitating the PTCA procedure by making it easier for the radiologist to integrate opacified (or "roadmap") information with real-time fluoroscopic information. The roadmap information shows information relating to the patient's circulatory system, while the fluoroscopic information shows information relating to the balloon catheter and its positioning with respect to the patient's skeletal system.

In PTCA, an inflatable catheter is introduced into the patient's circulatory system and guided to a stenosis (blockage) in the patient's heart. When the catheter is properly positioned, it is inflated to a greatly increased size and brought to bear against the stenosis. This causes the stenosis to be flattened against the arterial wall, clearing the artery and thereby improving blood flow through it.

Prior art X-ray equipment does not provide a convenient way for the radiologist to evaluate the success of the PTCA procedure. Conventionally, the radiologist does not objectively know, during the course of the PTCA procedure, whether the stenosis has been sufficiently flattened. The radiologist must judge the success of the operation subjectively. Thus, the radiologist may repeatedly inflate the balloon catheter when the stenosis has already been broken up, just to be sure that the catheter is not prematurely withdrawn from the patient's body. This additionally may prolong the procedure unnecessarily and is undesirable because the catheter remains in the heart when this is not strictly necessary.

One object of the invention is to provide a device which is usable by a radiologist during a PTCA procedure.

Another object of the invention is to provide a device which is usable by a radiologist in the sterile conditions of a catheterization laboratory while the radiologist is standing at the patient's bedside.

Still another object of the invention is to provide a device which allows a radiologist to compare arterial blood flow before and after the PTCA procedure so as to avoid, on the one hand, unnecessary inflation(s) of the balloon catheter, and on the other hand, premature withdrawal of the balloon catheter from the patient's body.

Yet another object of the invention is to provide a device which allows the radiologist to compare the dynamic motion of the heart both before and after the PTCA procedure so as to be better able to evaluate the improvement in heart performance after the procedure.

SUMMARY OF THE INVENTION

In accordance with the invention, there is provided to the radiologist for comparison purposes a depiction of the blood flow through the arterial region of interest both before and after the PTCA procedure. This is done by displaying, advantageously in a side-by-side manner on a single video monitor, "before" and "after" opacified images, synchronized with the patient's electrocardiogram.

The invention proceeds from the well-known fact that the width of the opacified image at the stenosis corresponds to the diameter of the unblocked portion of the artery. Thus, if it were possible to display, side-by-side, comparable "before" and "after" opacified images of the stenotic area, the ratio of the widths of the "before" and "after" opacified images at the stenosis would represent the improvement which has been achieved by the PTCA procedure. Additionally, if such a display were possible, the radiologist would be able to compare dynamic action of the heart both before and after the PTCA procedure. This comparison is diagnostically significant, because the degree of blood flow through the heart affects heart function.

Such a display has not heretofore been possible, because the opacified images change cyclically with the patient's heartbeat. As a result, it has previously been impossible to compare "before" and "after" opacified images because there has previously been no way to be sure that both images are derived from the same portion of the patient's cardiac cycle.

In accordance with the invention, a first series of video frames of the opacified image in the stenotic area are taken before the procedure is carried out, while monitoring and storing the patient's electrocardiogram. After the procedure has been carried out, a second series of video frames of the opacified image in the stenotic area are taken, likewise while monitoring and storing the patient's electrocardiogram. The electrocardiogram information is correlated to the video information.

Because the patient's heartbeat is not metronomically regular, one of the series, (advantageously but not necessarily the second series) is either elongated or truncated at appropriate places by addition or deletion of video frames so that the "heartbeats" in the second series are made to be substantially identical in duration to the corresponding heartbeat intervals in the patient's "before" electrocardiogram. Then, the first series and the modified second series of frames are displayed simultaneously, advantageously on a split-screen monitor. The display is synchronized and when the complete series have been displayed, the display is repeated. Therefore, the radiologist is presented with two comparable opacified images of the same stenotic area, one representing the status of the stenosis and the dynamic action of the heart before the PTCA procedure and the other representing the status of the stenosis and the dynamic action of the heart afterward.

BRIEF DESCRIPTION OF THE DRAWINGS

Exemplary and non-limiting preferred embodiments of the invention are shown in the drawings, in which:

FIG. 2A and 2B schematically illustrate the basic principle by which the effectiveness of a PTCA procedure may be evaluated;

DETAILED DESCRIPTION OF PREFERRED EMBODIMENTS

Figure 1:
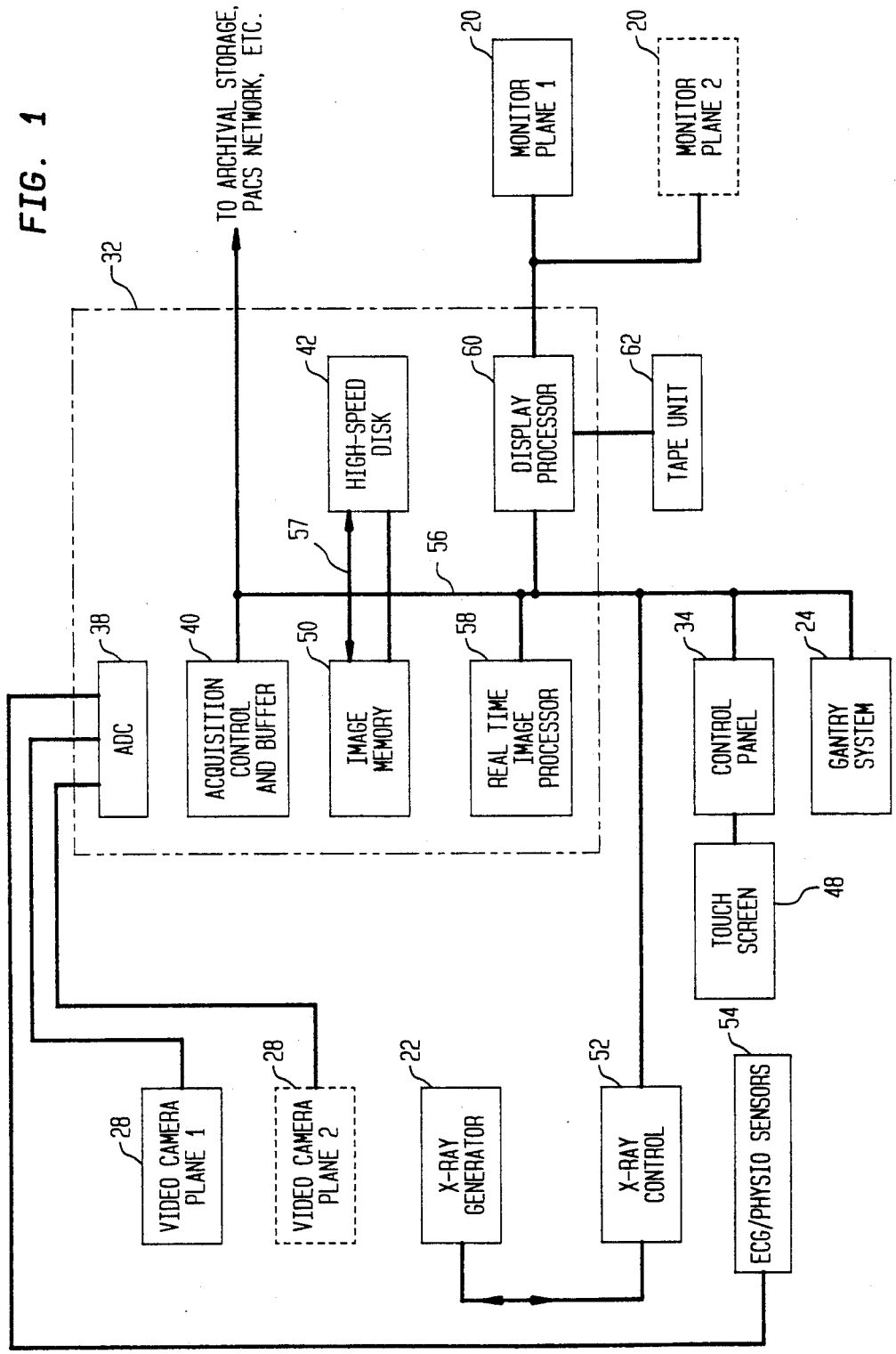
FIG. 1 schematically illustrates a block diagram of the preferred embodiment of the invention.

Referring initially to FIG. 1, and with reference to the above-referenced parent application, video image frames of the region of interest in the patient (not shown) are generated by a video camera 28 and, after passing through an analog-to-digital converter 38 and acquisition control and buffer circuitry 40, stored on a high-speed disk 42. This image information is associated with the position of the gantry system 24 at which the information is acquired and this position information is also stored on the disk 42. Simultaneously with acquisition of this image information, electrocardiogram and physiological information about the patient is acquired by ECG/PHYSIO sensors 54 and likewise stored on the disk 42.

As will be seen below, this information, if acquired under the appropriate circumstances, can be used to objectively indicate the success of a particular PTCA procedure. With this information, the radiologist can determine whether subsequent inflation(s) of the balloon catheter (not shown) are necessary or whether the balloon catheter can be withdrawn from the patient's body.

The principle of this success determination is illustrated in FIG. 2. FIG. 2A shows an opacified image of an artery 100 with a stenosis 102 therein. The stenosis 102 is not visible directly, but it constricts blood flow and therefore is manifested by the reduced width of the opacified image at the stenosis. FIG. 2B shows an opacified image of the same artery 100, but after the stenosis 102 has been removed by PTCA. It will be immediately apparent that the improvement achieved by the PTCA procedure can be expressed as the ratio of the post-PTCA diameter 104 to the pre-PTCA diameter 106.

In the past, it has not been possible to produce comparable pre-and post-PTCA images such as are shown in FIG. 2. This is because the diameter of the artery 100 changes during the patient's cardiac cycle. Only if the pre- and post-PTCA images are taken at the same point in the patient's cardiac cycle will the images be usable to illustrate the success of the PTCA procedure. In substance, the preferred embodiment of the invention produces two images which are synchronized with each other and which represent pre- and post-PTCA images. A comparison of these two images makes it possible to objectively determine the degree of success of a PTCA procedure.

Before the balloon catheter is inflated, a first series of video frames are taken of the opacified image of the stenotic area while monitoring the patient's electrocardiogram. The first series of frames is stored in association with the patient's electrocardiogram and consequently can be associated with the patient's cardiac cycle. In a typical case, the first series will last for approximately five seconds, accounting for perhaps six heartbeats at fifteen video frames per second, but this is not a part of the invention: both the frame rate and the duration of the first series can be changed.

After inflation(s) of the balloon catheter, dye is injected into the patient's bloodstream and a second series of video frames is taken of the opacified image of the stenotic area while monitoring the patient's electrocardiogram. The viewing angle of the camera 28, the frame rate, and advantageously the duration of the second series of video frames are chosen to be identical to the viewing angle, the frame rate and the duration of the first series of video frames.

Figure 3:
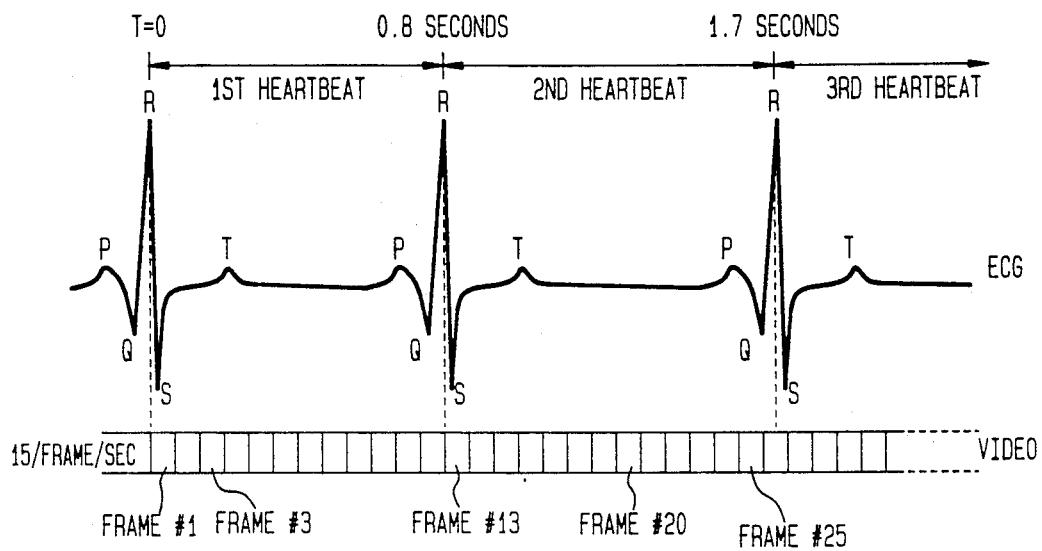
FIG. 3 schematically illustrates the acquisition of a first series of video frames of an opacified image of a stenotic region, together with the patient's electrocardiogram, before performance of the PTCA procedure.
Figure 4:
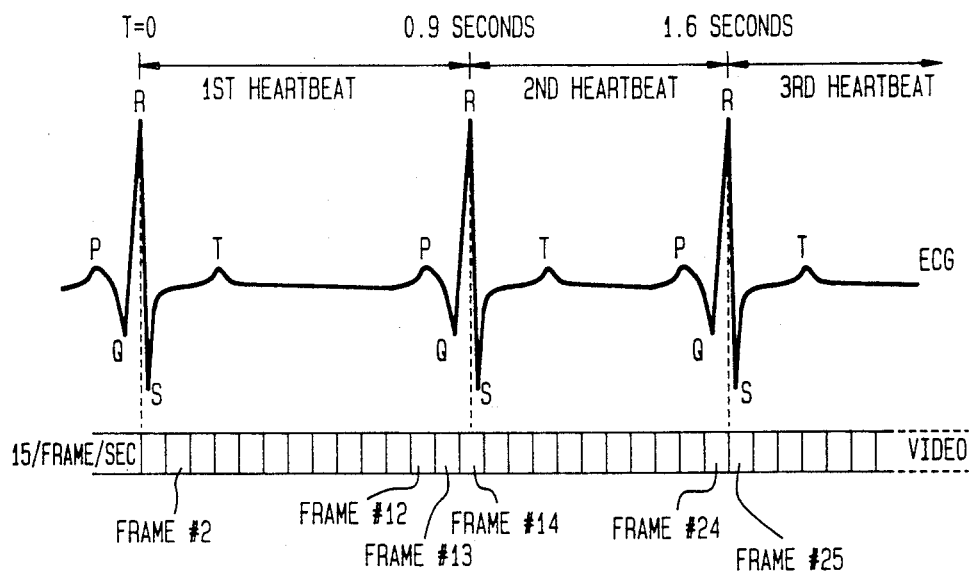
FIG. 4 schematically illustrates the acquisition of a second series of video frames of an opacified image of the stenotic region, together with the patient's electrocardiogram, after performance of the PTCA procedure.

As can be seen in FIGS. 3 and 4, the patient's cardiac cycle is not metronomic. Consequently, if the first and second series of video frames were to be displayed side-by-side on a monitor, the resulting images would not be synchronized. Thus, in accordance with the invention, the second series of video frames is modified so as make the "heartbeats" in the modified second series identical in duration to the heartbeats in the first series.

Figure 5:
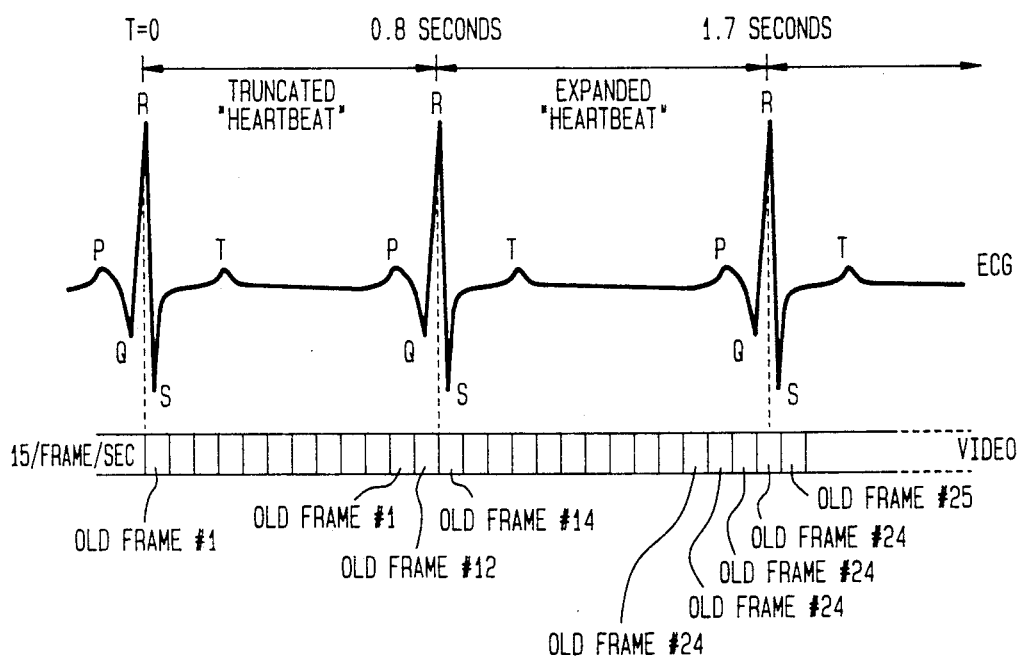
FIG. 5 schematically illustrates the operation of the preferred embodiment of the invention, wherein the second series is modified prior to cyclical display together with the first series.

The modification is carried out by either adding or deleting video frames to the end of each of the cardiac cycles. For example, it will be apparent that the patient's heart was beating more slowly at the beginning of the second series than at the beginning of the first series. Therefore, the duration of the first cardiac cycle in the second series is longer than the duration of the first cardiac cycle in the first series. The time difference—in this example, 0.1 seconds—corresponds to 1.5 frames. Thus, the second series of video frames is modified by eliminating therefrom, prior to display, frame 13 On display (s ® ®FIG. 5), frame 14 is displayed immediately after frame 12.

However, it can be seen that the second heartbeat during the second series was faster than the second heartbeat during the first series. Thus, the duration (0.7 sec) of the second cardiac cycle in the second series is shorter than the duration of the second cardiac cycle in the first series (0.9 sec). The time difference—in this example, 0.2 seconds—corresponds to three frames. Thus, the second series of video frames is modified by adding thereto, prior to display, three frames between frames 24 and 25. This is implemented by repeating frame 24 an additional three times before displaying frame 25.

After this modification of the second series, the frames at the beginning of each cardiac cycle in the modified second series relate to the same points in the cardiac cycle as do the frames at the beginning of each cardiac cycle in the first series. Another way of stating this is that the two series of frames are synchronized to the R-waves in the patient's pre-PTCA electrocardiogram. Consequently, when the second series, as modified, is repeatedly displayed side by side with the unmodified first series on a monitor, the radiologist can see comparable "before" and "after" images and can determine whether the stenosis has been sufficiently flattened. The radiologist can also determine the degree of improvement in the dynamic action of the heart, as caused by the increased blood flow through it.

The video images at the end of each cardiac cycle in the second series as modified do not always correspond to that which occurred in real time because actual data is either discarded or additional data is inserted. However, this is in practice not disadvantageous, because almost all of the heart motion occurs at the beginning of the cardiac cycle and the added/discarded data relates to the resting phase of the heart. Thus, little diagnostic error is caused by insertion and deletion of video information at the end of a cardiac cycle and before the beginning of the next cardiac cycle.

When, after the performance of the PTCA procedure and before the balloon catheter has been withdrawn from the patient's body, the radiologist wishes to compare blood flow through the previously blocked arterial region after the procedure with the flow before the procedure. Dye is injected and an opacified image run, along with associated gantry position and electrocardiogram values, is taken and stored. Then, the PRE/POST COMPARE mode is enabled by touching an appropriate area on the touch screen 48 on the control panel 34. The image processor 58 then causes the before and after (PRE and POST) runs to be displayed on the monitor 20 in a split-screen mode, where the two sets of images are synchronized as described above.

Thus, the radiologist can examine side by side the blood flow through the arterial region of interest before and after performance of the PTCA procedure. This can be done without fully removing the catheter so that in the event that the procedure was not sufficiently effective, the radiologist can easily repeat it.

In the preferred embodiment, it is the second series which is modified by addition and deletion of video frames. This is because the first series has already been taken and it is convenient to use the first series as the R-wave benchmark. However, although this is preferred, it is not necessary. It would alternatively be possible to modify the first series rather than the second series.

Furthermore, while it is advantageous if the first and second series have approximately the same duration, this is not absolutely necessary. If the pre-PTCA series is, e.g. ten heartbeats long and the post-PTCA series is, e.g. six heartbeats long, the invention can be practiced by producing a modified series which is six heartbeats long and ignoring the four least significant cardiac cycles in the pre-PTCA series. Also, for purposes of display, the radiologist should see a cyclic display of an integral number of cardiac cycles which represent contrast influx and out-flux. As a matter of practice, a display of approximately six full cardiac cycles is presently preferred because it contains the most significant cardiac data. This is because any one cycle may be atypical and an inappropriate basis upon which to make a clinical decision about the success of the PTCA procedure.

Those skilled in the art will understand that changes can be made in the preferred embodiments here described, and that these embodiments can be used for other purposes. Such changes and uses are within the scope of the invention, which is limited only by the claims which follow.

I claim:

1. A method for displaying comparable images of a stenotic area in a patient's artery both before and after a percutaneous transluminal coronary angioplasty (PTCA) procedure, comprising the steps of:
   acquiring, while monitoring and storing the patient's electrocardiogram, a first series of video frames of a opacified image of the stenotic area before the PTCA procedure has been carried out, said first series lasting for at least two complete cardiac cycles and being correlated with said electrocardiogram;
   acquiring, while monitoring and storing the patient's electrocardiogram, a second series of video frames of a opacified image of the stenotic area after the PTCA procedure has been carried out, said second series lasting for at least two complete cardiac cycles, being correlated with said electrocardiogram and being taken at an angle of view which is identical to the angle used while acquiring said first series of video frames; and
   modifying one of said series by changing the number of video frames at the end of each cardiac cycle in such a manner as to produce a modified series in which each of the cardiac cycles is as long as a corresponding one of the cardiac cycles in the other one of said series.

2. The method of claim 1, further comprising the step of repeatedly displaying, adjacent each other, said modified one of the series and said another one of the series.

3. The method of claim 1 wherein the second series is modified.

4. The method of claim 1 wherein said modifying step is carried out by deleting video frames where deletion is necessary and by copying a last frame in a cardiac cycle where addition is necessary.

5. Apparatus for displaying comparable images of a stenotic area in a patient's artery both before and after a percutaneous transluminal coronary angioplasty (PTCA) procedure, comprising:
   means for acquiring, while monitoring and storing the patient's electrocardiogram, a first series of video frames of a opacified image of the stenotic area before the PTCA procedure has been carried out, said first series lasting for at least two complete cardiac cycles and being correlated with said electrocardiogram;
   means for acquiring, while monitoring and storing the patient's electrocardiogram, a second series of video frames of a opacified image of the stenotic area after the PTCA procedure has been carried out, said second series lasting for at least two complete cardiac cycles, being correlated with said electrocardiogram and being taken at an angle of view which is identical to the angle used while acquiring said first series of video frames; and
   means for modifying a one of said series by changing the number of video frames at the end of each cardiac cycle in such a manner as to produce a modified series in which each of the cardiac cycles is as long as a corresponding one of the cardiac cycles in the other one of said series.

6. The apparatus of claim 5, further comprising means for displaying, adjacent each other, said modified one of the series and said another one of the series.

7. The apparatus of claim 6, wherein said displaying means is a video monitor.

8. The apparatus of claim 5, wherein said modifying means operates in such a manner as to modify the second series.

9. The apparatus of claim 5, wherein said modifying means operates in such a manner as to delete video frames where deletion is necessary and by copying the last frame in a cardiac cycle where addition is necessary.

* * * * *